(12) United States Patent
Maciejewski (10) Patent No.: US 9,910,110 B2
(45) Date of Patent: Mar. 6, 2018

(54) MEDICAL IMAGING DEVICE COMPRISING A HOUSING UNIT THAT HAS A CASING SHELL AND METHOD FOR PRODUCING A CASING SHELL OF THE MEDICAL IMAGING DEVICE

(71) Applicant: Siemens Healthcare GmbH, Erlangen (DE)

(72) Inventor: Bernd Maciejewski, Markt Erlbach (DE)

(73) Assignee: Siemens Healthcare GmbH, Erlangen (DE)

( * ) Notice: Subject to any disclaimer, the term of this patent is extended or adjusted under 35 U.S.C. 154(b) by 1369 days.

(21) Appl. No.: 13/753,977

(22) Filed: Jan. 30, 2013

(65) Prior Publication Data

US 2013/0200896 A1 Aug. 8, 2013

(30) Foreign Application Priority Data

Feb. 2, 2012 (DE) .................. 10 2012 201 485

(51) Int. Cl.
*G01R 33/28* (2006.01)
*G01R 33/38* (2006.01)
G01R 33/385 (2006.01)
A61B 6/03 (2006.01)

(52) U.S. Cl.
CPC .......... *G01R 33/28* (2013.01); *G01R 33/3802* (2013.01); *A61B 6/035* (2013.01); *G01R 33/3854* (2013.01)

(58) Field of Classification Search
CPC ............... G01R 33/28; G01R 33/3802; G01R 33/3854; A61B 6/035
See application file for complete search history.

(56) References Cited

U.S. PATENT DOCUMENTS

| | | | | |
|---|---|---|---|---|
| 3,832,135 A | * | 8/1974 | Drozdowski et al. | G01N 5/028 141/130 |
| 4,755,754 A | * | 7/1988 | Sireul | G01R 33/3854 324/318 |
| 4,811,375 A | * | 3/1989 | Klostermann | H01J 35/101 378/121 |
| 5,657,369 A | * | 8/1997 | Stein | A61B 6/0421 378/195 |
| 5,717,735 A | * | 2/1998 | Ramsdell | A61B 6/0421 378/195 |

(Continued)

FOREIGN PATENT DOCUMENTS

| | | |
|---|---|---|
| DE | 19838390 A1 | 3/2000 |
| DE | 102007037851 A1 | 2/2009 |
| DE | 102011082402 A1 | 3/2013 |

OTHER PUBLICATIONS

Calfee-Bilder; http://www.spiegel.de/auto/aktuell/neue-werkstoffe-im-fahrradbau-bambus-statt-blech-a-667888.html; Others; 2010.

*Primary Examiner* — Dixomara Vargas
(74) *Attorney, Agent, or Firm* — Schiff Hardin LLP (57) ABSTRACT

A medical imaging device is presented. The medical image device includes a detection unit and a housing unit that surrounds the detection unit. The housing unit has at least one casing shell. The at least one casing shell includes a netlike supporting structure unit and an elastic spring-mass unit. The netlike supporting structure unit is at least partially embedded within the elastic spring-mass unit.

12 Claims, 3 Drawing Sheets

(56) References Cited

U.S. PATENT DOCUMENTS

| | | | | |
|---|---|---|---|---|
| 5,748,705 | A * | 5/1998 | Stein | A61B 6/0421 378/196 |
| 5,771,272 | A * | 6/1998 | Berger | A61B 6/0421 378/207 |
| 5,778,045 | A * | 7/1998 | von Stetten | A61B 6/0421 378/196 |
| 5,835,555 | A * | 11/1998 | Barry | A61B 6/0421 378/146 |
| 5,838,765 | A * | 11/1998 | Gershman | A61B 6/0421 378/146 |
| 6,009,147 | A * | 12/1999 | Stein | A61B 6/0421 378/146 |
| 6,160,399 | A * | 12/2000 | Radziun | G01R 33/385 324/319 |
| 6,169,400 | B1 * | 1/2001 | Sakuma | G01R 33/34053 324/318 |
| 6,414,489 | B1 * | 7/2002 | Dean | G01R 33/3854 324/318 |
| 6,437,568 | B1 * | 8/2002 | Edelstein | G01R 33/3854 324/309 |
| 6,882,152 | B2 * | 4/2005 | Schuster | G01R 33/3858 324/318 |
| 6,954,068 | B1 * | 10/2005 | Takamori | G01R 33/3854 324/318 |
| 7,084,629 | B2 * | 8/2006 | Monski, Jr. | G01R 33/34046 324/318 |
| 7,372,053 | B2 * | 5/2008 | Yamashita | A61N 5/10 250/398 |
| 7,378,848 | B2 * | 5/2008 | Gao | G01R 33/307 324/318 |
| 7,567,082 | B2 * | 7/2009 | Takamori | G01R 33/3854 324/318 |
| 7,980,356 | B2 | 7/2011 | Maciejewski | |
| 8,359,084 | B2 * | 1/2013 | Love | A61B 5/702 324/318 |
| 8,525,116 | B2 * | 9/2013 | Schulz | G01T 1/1603 250/363.02 |
| 8,615,368 | B2 * | 12/2013 | Light, II | C12Q 1/6851 702/20 |
| 9,488,704 | B2 * | 11/2016 | Hierl | G01R 33/28 |
| 9,535,145 | B2 * | 1/2017 | Demeester | A61B 6/037 |
| 9,538,963 | B2 * | 1/2017 | Smithanik | A61B 6/035 |
| 9,638,775 | B2 * | 5/2017 | Dietz | G01R 33/3854 |

* cited by examiner

MEDICAL IMAGING DEVICE COMPRISING A HOUSING UNIT THAT HAS A CASING SHELL AND METHOD FOR PRODUCING A CASING SHELL OF THE MEDICAL IMAGING DEVICE

CROSS REFERENCE TO RELATED APPLICATIONS

This application claims priority of German application No. 102012201485.3 DE filed Feb. 2, 2012. All of the applications are incorporated by reference herein in their entirety.

FIELD OF INVENTION

The disclosure relates to a medical imaging device comprising a detection unit and a housing unit which surrounds the detection unit and has at least one casing shell.

BACKGROUND OF INVENTION

Magnetic resonance devices output a high level of operating noise during operation, wherein said noise may have an unpleasant effect on a patient who is held in a locating region of the magnetic resonance device for the purpose of examination. This high level of operating noise is generated within a magnet unit of the magnetic resonance device due to an interaction of a gradient unit with a magnet. In this case, sound transmission within the magnetic resonance device occurs by means of airborne-sound excitation and via a solid-borne sound component. The high level of operating noise is thus transmitted to a housing unit of the magnetic resonance device, and radiated from said housing unit to a space surrounding the magnetic resonance device.

Conventional housing units of magnetic resonance devices have a housing unit which comprises casing shells that are made of e.g. glass-fiber reinforced plastic and/or a thermoplastic. These casing shells are screwed to a frame unit, for example, and/or screwed and/or connected directly to the magnets by means of corresponding retaining elements. Although these casing shells offer a degree of sound insulation by virtue of their mass, casing shells that are designed in this way also have a high radiation response in respect of radiation of soundwaves, said response being caused by a material stiffness of the casing shells.

SUMMARY OF INVENTION

A medical imaging device in which effective noise damping and/or noise separation is achieved in the housing unit is provided A method for producing, by timesaving and costsaving means, a noise-separated and/or noise-attenuating casing shell for a medical imaging device is further provided.

As a starting point a medical imaging device comprising a detection unit and a housing unit which surrounds the detection unit and has at least one casing shell.

It is proposed that the at least one casing shell should have a netlike supporting structure unit and an elastic spring-mass unit. By virtue of this embodiment, it is possible to achieve a damping and/or separation of soundwaves within the housing unit and thus minimize any radiation of soundwaves from the housing unit during operation of the medical imaging device, in particular a magnetic resonance device. Moreover, by virtue of the single-shell embodiment of the casing shell, it is possible to save additional costs and components, such as e.g. additional stiffening elements and/or stiffening units. It is also possible to produce a casing shell that is acoustically optimized. As a result of the netlike supporting structure unit, it is also possible to achieve a stiffening of the casing shell, which also has large vibration damping and/or airborne-sound absorbing surfaces and/or regions, thereby allowing particularly simple assembly of the casing shell. The medical imaging device may take the form of any medical imaging device deemed suitable by a person skilled in the art. However, the medical imaging device takes the form of a magnetic resonance device, since use of the sound damping and/or sound separating casing shell is particularly profitable here due to a significant noise exposure during measurement operations.

It is further proposed that the elastic spring-mass unit should have an element that absorbs airborne sound and a heavy mass element. In this type of configuration, it is possible to achieve a damping and/or separation of soundwaves as a result of high mass inertia and absorption of the vibrational energy of soundwaves. In this context, a heavy mass element is understood in particular to be an element that has a density (in particular a surface density) of at least 3 kg/m$^2$ and at most 8 kg/m$^2$, and in a further embodiment approximately 4 kg/m$^2$ to approximately 5 kg/m$^2$. The element for absorbing airborne sound may take the form of an elastic spring element, in particular a flexible foam, and is specifically designed to convert sound energy of soundwaves into a vibrational energy of inaudible vibrational waves, and to reduce or prevent a reflection of audible soundwaves at a boundary surface accordingly. As part of this activity, the soundwaves (in particular airborne soundwaves) cause individual particles of the airborne-sound absorbing element to vibrate, wherein a vibrational energy that is generated within the airborne-sound absorbing element is converted into thermal energy. In this way, a vibrational energy is removed from the soundwaves (in particular the airborne soundwaves) and the airborne soundwaves are damped. The elastic spring-mass unit may also be so designed as to be resistant to bending, wherein a resonant frequency of the elastic spring-mass unit may be configured as to be higher than 3000 Hz and in a further embodiment higher than 5000 Hz, such that the resonant frequency of the elastic spring-mass unit is outside of a frequency range that is relevant for a noise transmission within the medical imaging device. In this context, the heavy mass element may be arranged on a side of the casing shell that faces away from the detection unit and the airborne-sound absorbing element may be arranged on a side of the casing shell that faces towards the detection unit in an assembled position on the medical imaging device.

The casing shell may be produced in a particularly simple and inexpensive manner if the heavy mass element is composed at least partly of an integral foam and/or from a material that is made of a renewable raw material. In this context, an integral foam is understood in particular to be a foam that may have a closed outer skin and a core, wherein a density of the integral foam decreases in the direction from the closed outer skin to the core. The material that is made of the renewable raw material may be composed of e.g. a natural rubber and/or other renewable raw material deemed suitable by a person skilled in the art. The integral foam and/or the material that is made of a renewable raw material may have a Shore A hardness between 50 and 60 in this context, and in a further embodiment a Shore A hardness of approximately 55, such that a sufficient degree of stiffness at the same time as softness for the purpose of soundwave damping is available for the casing shell. Alternatively or additionally, the heavy mass element may also be composed of a dense mat that is made of a polyurethane foam vinyl film and/or other materials deemed suitable by a person skilled in the art. It is thus possible to realize a particularly stable spring-mass unit, which covers the detection unit and provides a protection against contact between the casing unit and mechanically moving components and/or electrical components of the detection unit. The heavy mass element that may be composed of the integral foam so designed as to withstand a compressive force of at least 25 kg using a test probe having a diameter of 30 mm.

A particularly compact casing shell may be achieved if the heavy mass element is arranged in the form of a layer within the casing shell and has a layer thickness of 2 mm to 5 mm, and in a further embodiment of 2 to 4 mm.

In an embodiment, it is proposed that the netlike supporting structure should be so arranged as to be at least partially embedded within the airborne-sound absorbing element, whereby the netlike supporting structure unit may be connected and/or fixed to the elastic spring-mass unit in a structurally simple manner within the casing shell.

In an embodiment, the airborne-sound absorbing element may have a layer that is arranged between the heavy mass element and the netlike supporting structure unit, said layer having a thickness of approximately 3 mm, whereby it is possible to achieve an adhesive property of the soft foam layer in relation to the heavy mass element and the netlike supporting structure unit. In order to achieve the adhesive property, however, the thickness of the airborne-sound absorbing element should be at least approximately 3 mm, since an adhesive property of the airborne-sound absorbing element decreases in the case of thicknesses of less than approximately 3 mm. Moreover, a thickness of approximately 3 mm of the airborne-sound absorbing element allows an optimum to be achieved in respect of stability of the airborne-sound absorbing element.

It is further proposed that the casing shell should have at least one region that is arranged between supporting structure elements that are comprised in the netlike supporting structure unit, said region being filled by the airborne-sound absorbing element, whereby unwanted deformation of the casing shell and in particular of the netlike supporting structure unit may be achieved during curing in the production of the casing shell, in particular during foaming of the netlike supporting structure unit. In addition to a function of soundwave damping and/or soundwave separation, the airborne-sound absorbing element in this hollow space may also have a function of additional stabilization during curing, e.g. after foaming the netlike supporting structure unit, such that stresses occurring during a reaction process and/or a curing process, in particular contraction stresses of the netlike supporting structure unit, may be absorbed by the airborne-sound absorbing element and a shape and/or a design of the netlike supporting structure unit and/or of the casing shell is retained.

It is further proposed that the netlike supporting structure unit should have an integrated shape, whereby the netlike supporting structure unit may already contribute to a damping of soundwaves, in particular solid-borne soundwaves, due to its shape-related elasticity.

In a further embodiment, it is proposed that the netlike supporting structure unit should be composed at least partially of an integral foam and/or a material that is made of a renewable raw material. The integral foam and/or the material that is made of a renewable raw material may have a Shore A hardness of approximately 65 to 70. By virtue of this embodiment, it is possible to achieve a stiffness of the netlike supporting structure unit, which also has an elasticity in respect of an absorption and/or damping of solid-borne soundwaves as a result of the netlike construction and choice of material. The material that is made of a renewable raw material may comprise lignin and/or bamboo and/or rattan, for example. Alternatively or additionally, it is also conceivable for the netlike supporting structure unit to comprise further materials such as e.g. a glass fiber reinforced plastic and/or a thermoplastic, etc.

An inexpensive casing shell providing protection against external effects and hence a robustness of the casing shell may be achieved if the casing shell has least one protective outer layer, which is arranged on a side of the spring-mass unit, in particular of the heavy mass element, that faces away from the detection unit. By attaching the protective outer layer to the spring-mass unit, it is also possible to dispense with an additional surface treatment for finishing the casing shell, such that costs and assembly time may also be saved in this way. The protective outer layer may be composed of a film and/or an artificial leather and/or other layers deemed suitable by a person skilled in the art.

At the same time as a robustness of the casing shell, a elasticity of the casing shell may be achieved if the casing shell has a shape that curves outwards. The outwards curving shape may be provided by the netlike supporting structure unit.

It is further proposed that the casing shell should have at least one peripheral region comprising a sealing element, whereby the casing shell may be sealed in relation to noise separation and/or soundwave damping at the peripheral region of the casing shell. The sealing element may extend along an entire length of the peripheral region. The sealing element may be molded onto e.g. the heavy mass element during production in this case, such that the sealing element may be produced in a structurally simple and particularly inexpensive manner. The sealing element and the heavy mass element may also be designed as a unitary part. It is also conceivable for the sealing element to be glued onto the heavy mass element, e.g. in the way that weatherstrips are glued on.

The methods also takes as its starting point a method for producing a casing shell for a housing unit of a medical imaging device, wherein the casing shell has a netlike supporting structure unit and an elastic spring-mass unit comprising a heavy mass element and an airborne-sound absorbing element. The method for producing the casing shell comprises the following method steps:
    foaming the heavy mass element,
    foaming the airborne-sound absorbing element, and
    attaching the netlike supporting structure to the heavy mass element and/or to the airborne-sound absorbing element.

By this means, the casing shell may be produced inexpensively and in particular rapidly with short manufacturing times. Moreover, the casing shell may also be produced in a particularly environmentally friendly manner, in particular if materials made of renewable raw materials are used, e.g. natural rubber and/or bamboo, etc. It is also possible to provide a particularly light casing shell for the housing unit. The foaming of the heavy mass element and the foaming of the airborne-sound absorbing element may take place sequentially in a single mould. The attachment of the netlike supporting structure unit may also take place in this mould, thereby avoiding further production steps. The netlike supporting structure unit may be attached by means of foaming the netlike supporting structure unit and/or by introducing and/or inserting a prefabricated netlike supporting structure unit.

It is further proposed that in a further method step a protective outer layer should be deposited on the heavy mass element, such that a protection of the casing shell is achieved. The protective outer layer may be composed of a lacquer coating, for example, which is deposited on the heavy mass element after the foaming of the heavy mass element and the foaming of the airborne-sound absorbing element and the introduction of the netlike structure element. For this purpose, the previously foamed casing shell may be removed from the mould that is used for foaming at least subcomponents of the casing shell.

In an embodiment, it is proposed that the protective outer layer should be introduced into the mould before any foaming and/or before introducing the heavy mass element into a mould for producing the casing shell, whereby the casing shell may be produced in a particularly time-saving and cost-saving manner by dispensing with further production steps. The protective outer layer here may be composed of a deep-drawable film, for example, which may be stretched in two directions that are orthogonal relative to each other, and/or an artificial leather layer, which is introduced into the mould before foaming of the heavy mass element. Further embodiments of the protective outer layer are readily conceivable.

It is moreover proposed that, in the step for attaching the netlike supporting structure unit, the netlike supporting structure unit should be foamed, thereby allowing the casing shell to be produced in a particularly inexpensive manner. Alternatively, the netlike supporting structure unit may also be prefabricated and this prefabricated netlike supporting structure unit may be attached to the heavy mass element and/or to the airborne-sound absorbing element, e.g. by foaming-in of the netlike supporting structure unit using the heavy mass element and/or the airborne-sound absorbing element. In this context, the netlike supporting structure unit may be composed of a glass-fiber reinforced plastic and/or a thermoplastic and/or a material that is made of a renewable raw material.

BRIEF DESCRIPTION OF THE DRAWINGS

Further features and details are derived from the embodiments described below and with reference to the drawings, in which.

DETAILED DESCRIPTION OF INVENTION

Figure 1:
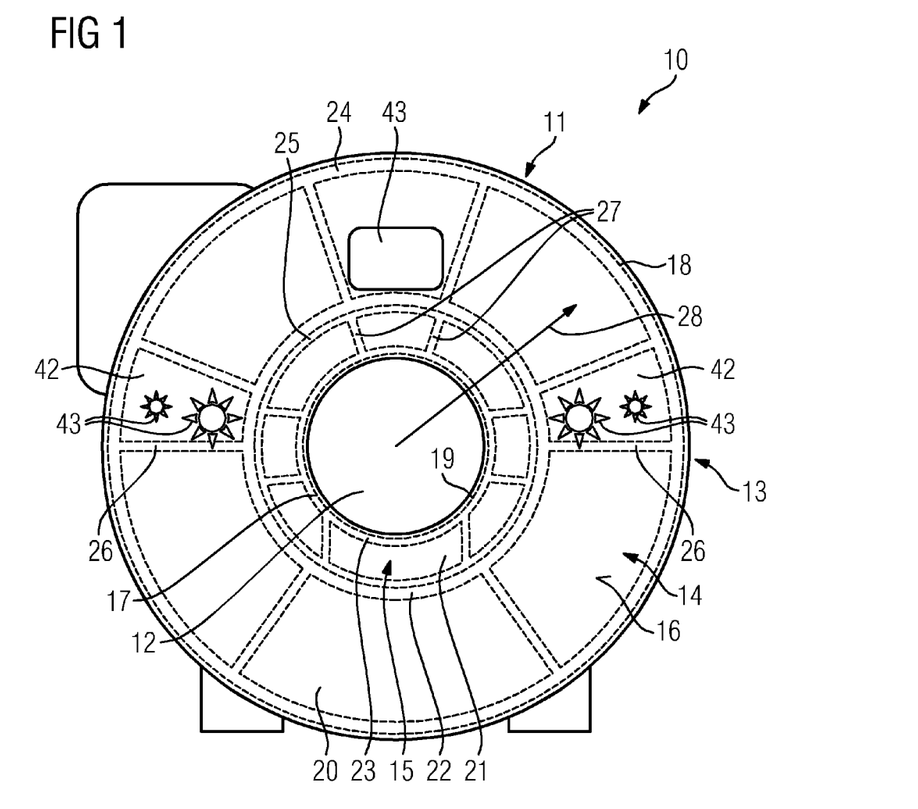
FIG. 1 shows a schematic representation of a medical imaging device with a casing shell.

A medical imaging device is schematically illustrated in FIG. 1 in the form of a magnetic resonance device 10. In an alternative embodiment, the medical imaging device may also take the form of a computer tomography device, a PET (positron emission tomography) device, etc.

The magnetic resonance device 10 comprises a detection unit in the form of a magnet unit 11, with a main magnet (not shown) for generating a strong and in particular constant main magnetic field. The magnetic resonance device 10 also has a locating region 12 for locating a patient, said locating region 12 being surrounded in a circumferential direction by the magnet unit 11. The patient may be pushed into the locating region 12 by means of a patient couch (not shown) of the magnetic resonance device 10. An arrangement and/or embodiment of the magnet unit 11 and/or of the locating region 14 may however vary from the arrangement and embodiment represented here.

The magnet unit 11 also has a gradient coil (not shown) for generating magnetic field gradients that are used for spatial encoding during imaging. The magnet unit 11 also has a high-frequency antenna unit (not shown) for exciting a polarization that occurs in the main magnetic field generated by the main magnet.

Furthermore, the magnetic resonance device has a housing unit 13 that surrounds the magnet unit 11. The housing unit 13 has a plurality of casing shells 14, 15, comprising a casing shell 14 for a front side 16 of the magnetic resonance device 10 and a casing shell 15 for an insertion funnel for an entrance opening 17 of the locating region 12 in the present embodiment. In this context, a complete housing casing for the front side 16 is composed of a single casing shell 14. The complete insertion funnel is likewise composed of a single casing shell 15. An alternative embodiment of the casing shells 14, 15 is readily possible, e.g. a casing shell for a rear side of the magnetic resonance device 10 and/or a casing shell for a side casing of the magnetic resonance device 10.

The casing shells 14, 15 have a netlike supporting structure unit 18, 19 and an elastic spring-mass unit 20, 21 in each case. As shown in FIG. 1, the netlike supporting structure units 18, 19 of the casing shells 14, 15 have an inner supporting ring 22, 23 and an outer supporting ring 24, 25 in each case. In addition to this, the netlike supporting structure units have a plurality of connecting braces 26, 27 in each case, which connect the inner supporting ring 22, 23 to the outer supporting ring 24, 25 for each of the casing shells 14, 15. The connecting braces 26, 27 are so arranged as to extend in a radial direction 28 outwards from the entrance opening 17 of the locating region 12. The netlike supporting structure units 18, 19 therefore provide an integrated shape for each of the casing shells 14, 15.

Figure 2:
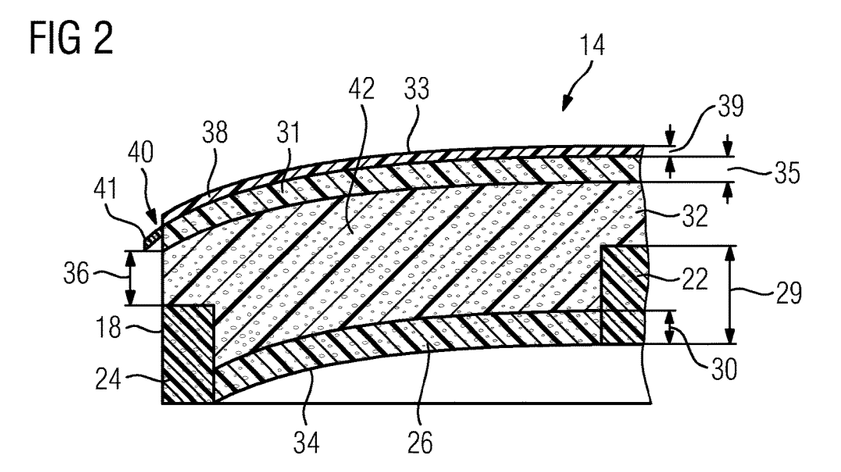
FIG. 2 shows a sectional view of a first embodiment of a casing shell.

Furthermore, the netlike supporting structure units 18, 19 for each of the casing shells 14, 15 have a shape that curves outwards (FIG. 2). The casing shells 14, 15 therefore have a convex shape as seen from the outside. By virtue of this convex shape and the continuous annular shape of the netlike supporting structure unit 18, 19, the casing shells 14, 15 already have a noise damping and/or soundwave damping effect, particularly in respect of solid-borne soundwaves, when the magnetic resonance device 10 is operating. In principle, the casing shells 14, 15 may also have a non-convex construction, e.g. for the purpose of covering and/or casing surfaces that are not curved.

In the present embodiment, the netlike supporting structure units 18, 19 are composed in each case of an integral foam having a Shore A hardness of approximately 65 to 70, such that the netlike supporting structure units 18, 19 provide a sufficiently high degree of stability for the casing shells 14, 15. The inner supporting rings 22, 23 and the outer supporting rings 24, 25 have a thickness 29 of approximately 10 mm in each case. By contrast, the connecting braces 26, 27 have a lesser thickness 30 than the thickness 20 of the inner supporting rings 22, 23 and of the outer supporting rings 24, 25. The thickness 30 of the connecting braces 26, 27 is approximately 4 mm in the present embodiment (FIG. 2).

The casing shell 14 of the front side of the housing unit 13 is shown by way of example in FIG. 2 and is described in greater detail below. However, the casing shell 15 has a similar structure.

The elastic spring-mass unit 20 of the casing shell 14 has a heavy mass element 31 and an airborne-sound absorbing element 32. The heavy mass element 32 is arranged on a side 33 of the casing shell 14 that faces away from the magnet unit 11 and the airborne-sound absorbing element 32 is arranged on a side 34 of the casing shell 14 that faces towards the magnet unit 11 (FIG. 2). In the present embodiment, the airborne-sound absorbing element 32 of the elastic spring-mass unit 20 is composed of a flexible foam that has a Shore A hardness from approximately 30 to a maximum of 40.

The heavy mass element 31 has a surface density of at least 3 $kg/m^2$ to at most 8 $kg/m^2$, or approximately 4 $kg/m^2$ to approximately 5 $kg/m^2$. In the present embodiment, the heavy mass element 31 is composed of an integral foam that has a Shore A hardness of 50 to 60, or a Shore A hardness of approximately 55. Furthermore, the heavy mass element 31 is arranged in the form of a layer within the casing shell 14, thereby forming a heavy mass layer. A layer thickness 35 of the heavy mass layer is between 2 mm and 5 mm in this case. For a layer thickness 35 of approximately 2 mm, the surface density of the heavy mass element is approximately 4 $kg/m^2$. The heavy mass layer is sufficiently stable in design by virtue of its integral foam construction, such that the heavy mass element 31 withstands a compressive force of at least 25 kg acting on the heavy mass element 31 using a test probe having a diameter of 30 mm as per IEC standard 60601-3.

By virtue of the Shore A hardness of 50 to 60 of the heavy mass element 31, stability and strength of the casing shell 14 are essentially created by a combination and/or an interaction of the netlike supporting structure unit 18 with the heavy mass element 31. Intervals between the connecting braces 26 within the casing shell 14 cover an angular range of 50° to 60° in this case (FIG. 1). An interval between the connecting braces 26 is only reduced in regions of the casing shell 14 in which e.g. operating elements 43 are arranged. As shown in FIG. 1, the intervals between the connecting braces 27 of the casing shell 15 are not uniform.

The netlike supporting structure unit 18 is arranged on that side 34 of the casing shells 14, 15 which faces towards the magnet unit 11 and the heavy mass element 31 is arranged on that side 33 of the casing shells which faces away from the magnet unit 11 (FIG. 2). An additional layer of the airborne-sound absorbing element 32 is arranged between the layer of the heavy mass element 31 and the inner supporting ring 22, and between the layer of the heavy mass element 31 and the outer supporting ring 24. The layer of the airborne-sound absorbing element 32 has a layer thickness 36 of 3 mm, such that the airborne-sound absorbing element 32 is connected to the heavy mass element 31 and the inner supporting ring 22 and the outer supporting ring 24.

The casing shell 14 also has regions 37 that are situated between supporting structure elements of the netlike supporting structure unit 18. The supporting structure elements take the form of the inner supporting ring 22, the outer supporting ring 24 and the individual connecting braces 26, and therefore the regions 37 are situated between the inner supporting ring 22, the outer supporting ring 24 and the individual connecting braces 26. The regions 37 are filled with the airborne-sound absorbing element 32, such that the inner supporting ring 22, the outer supporting ring 24 and the individual connecting braces 26 are so arranged as to be at least partially embedded within the airborne-sound absorbing element 32. The airborne-sound absorbing element has a total thickness of at least 13 mm. In a further embodiment airborne-sound absorbing element has a total thickness 20 mm.

Furthermore, the casing shell 14 has a protective outer layer 38, which is arranged on a side of the heavy mass element 31 that faces away from the magnet unit 11 (FIG. 2). In the present exemplary embodiment, the protective outer layer 38 is composed of an artificial leather layer having a layer thickness 39 of approximately 1.5 mm. Alternatively, the protective outer layer 38 may also be composed of a lacquer coating and/or other material deemed suitable by a person skilled in the art.

The casing shell 14 also comprises a peripheral region 40, a sealing element 41 being arranged at the peripheral region 40 of the casing shell 14 (FIG. 2). The sealing element 41 is composed of a sealing lip and is arranged along an entire length of the peripheral region 40. The sealing element 41 may be designed as a unitary part with the heavy mass element 31 and/or with the airborne-sound absorbing element 32. The sealing element 41 may also be designed as a separate part. By virtue of the sealing element 41, the peripheral region 40 and/or edge region at which e.g. different casing shells 14, 15 meet is tightly sealed in relation to soundwave propagation.

The casing shell 14 has additional connecting braces 26 in regions 42 in which one or more operating elements 43 such as e.g. a display and/or a keyboard, etc. is arranged (FIG. 1), since the casing unit 14 is exposed to a greater load in these regions 42. These regions 42 also differ from the rest of the casing shell 14 in respect of an embodiment and/or arrangement of the elastic spring-mass unit 20. These regions 42 may have a second layer and/or shell of the elastic spring-mass unit 20 and the protective outer layer 38, wherein the second layer and/or shell comprises a layer of the airborne-sound absorbing element 32 and a layer of the heavy mass element 31 together with the protective outer layer 38. For the purpose of arranging the operating elements 43, the second layer and/or shell features cavities which have the dimensions of the operating elements 43 and within which the operating elements 43 are arranged.

In this case, the second layer and/or shell is mounted on a side 34 of the casing shell 14 that faces away from the magnet unit 11. The second layer and/or shell may be offset outwards in a stepped manner relative to the rest of the surface of the casing shell 14. It is also conceivable for the second layer and/or shell to form an integrated plane surface with the rest of the surface of the casing shell 14, and for a first layer and/or shell of the spring-mass unit 20 to be offset inwards in a stepped manner relative to the rest of the casing shell 14.

The operating elements 43 here take the form of input elements such as e.g. a keyboard and/or a touch screen, and output elements such as e.g. a monitor.

The casing shells 14, 15 also have fastening elements (not shown). These fastening elements take the form of catch elements, for example, such that simple engagement of the casing shells 14, 15 with frame elements of the housing unit 13 and/or with a further casing shell is possible. The fastening elements may be arranged on the inner supporting ring 22, 23 and/or the outer supporting ring 24, 25 of the netlike supporting frame unit 18, 19. The fastening elements may be already molded onto the inner supporting ring 22, 23 and/or the outer supporting ring 24, 25 of the netlike supporting frame unit 18, 19 during a production process.

Figure 3:
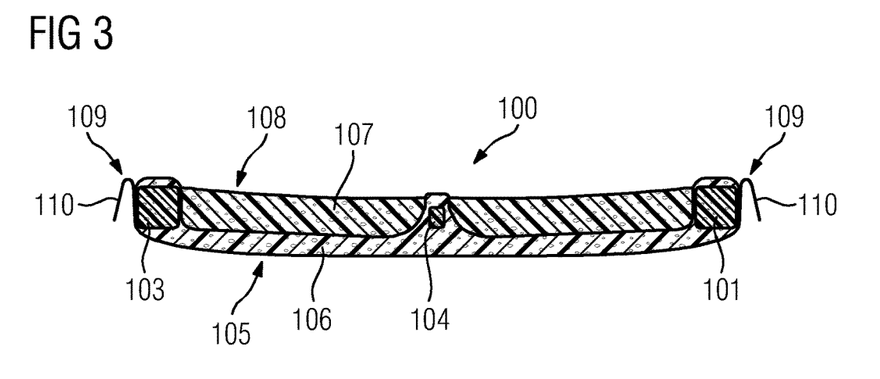
FIG. 3 shows a sectional view of an alternative embodiment, to that shown in FIG. 2, of a casing shell.

FIG. 3 shows an alternative embodiment of the casing shell 14, 15. Essentially identical components, features and functions are generally denoted by the same reference numbers. The following description is essentially limited to the differences in comparison with the embodiment in FIGS. 1 and 2, wherein reference is made to the description of the embodiment in FIGS. 1 and 2 with regard to identical components, features and functions.

FIG. 3 illustrates a section through an alternative embodiment of a casing shell 100 for a housing unit 13 of the magnetic resonance device 10. The casing shell 100 has a netlike supporting structure unit 101, which has an inner supporting ring, an outer supporting ring 103 and a plurality of connecting braces 104. In respect of its spatial arrangement, an embodiment of the netlike supporting structure unit 101 corresponds to the netlike supporting structure units 18, 19 as per the description relating to FIGS. 1 and 2. However, the netlike supporting structure unit 101 is composed of a thermoplastic that is produced using the injection molding method. Alternatively, the netlike supporting structure unit 101 may also be composed of an integral foam.

The casing shell 100 also has an elastic spring-mass unit 105, which has a heavy mass element 106 and an airborne-sound absorbing element 107. A material composition of the heavy mass element 106 and the airborne-sound absorbing element 107 likewise corresponds to the description of the embodiments as per FIGS. 1 and 2.

The inner supporting ring, the outer supporting ring 103 and the connecting braces 104 are so arranged as to be embedded within the heavy mass element 106. Regions 108 of the casing shell 100 between the inner supporting ring that is embedded in the heavy mass element 106, the outer supporting ring 103 that is embedded in the heavy mass element 106, and the connecting braces 104 that are embedded in the heavy mass element 106 are filled with the airborne-sound absorbing element 107. At its peripheral regions 109, the casing shell 100 has sealing elements 110 that are designed as a unitary part with the heavy mass element 106. Furthermore, the casing shell 100 also has a protective outer layer (not shown).

As an alternative to the embodiments presented here of the casing shells 14, 15, 100 as per FIGS. 1 to 3, the netlike supporting frame unit 18, 19, 101 may also be composed of a plastic such as e.g. a glass-fiber reinforced plastic and/or a thermoplastic, and/or of materials that are made of renewable raw materials such as e.g. lignin, bamboo and/or rattan. It is also possible for only partial regions of the netlike supporting frame unit 18, 19, 101 to be produced from the integral foam and for the rest of the netlike supporting frame unit 18, 19, 101 to be composed of a plastic or a material that is made of a renewable raw material. It is also conceivable for the elastic spring-mass unit 20, 21, 105, in particular the heavy mass element 31, 106 of the elastic spring-mass unit 20, 21, 105, to be constructed from a material other than the integral foam, e.g. from a PVC material and/or a commercial rubber-type material, and/or from materials that are made of renewable raw materials, e.g. natural rubber.

In an alternative embodiment of the casing shell 14, 15, 100, it is also possible for the dimensions of the netlike supporting structure unit 18, 19, 101 and the elastic spring-mass unit 20, 21, 105 to differ from the dimensions described in FIGS. 1 and 2. In particular, the netlike supporting structure unit 18, 19 may be composed solely of supporting braces that are mutually arranged in the form of a star, for example, and supporting rings within the netlike supporting structure unit 18, 19 may be omitted.

Figure 4:
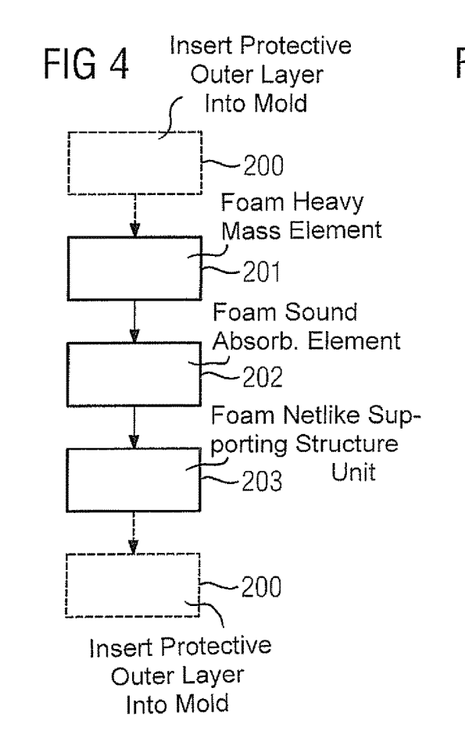
FIG. 4 shows a method for producing a casing shell.

FIG. 4 shows further details of a method for producing the casing shells 14, 15 that are described in FIGS. 1 and 2. A mould (not shown) is used for producing the casing shell 14, 15.

In a first step 200, the protective outer layer 38, e.g. the artificial leather layer and/or a thermoplastic and/or a deep-drawable film, etc., is first inserted into the mould. In a further step 201, the heavy mass element 31 is then foamed. During this activity, the mould is first closed and foam components are injected into the mould, these being foamed to the desired layer thickness 35 in this case.

After the heavy mass element 31 has been foamed, the airborne-sound absorbing element 32 is then foamed in a next step 202. For this purpose, the desired foam components are again introduced into the mould first, while a template that predefines the positions and/or regions of the netlike supporting structure unit 18, 19 within the casing shell 14, 15 is also inserted into the mould. The foaming of the soft foam of the airborne-sound absorbing element 32 then takes place.

In a further step 203, the netlike supporting structure unit 18, 19 is introduced into the mould. During this activity, the template that was used when foaming the airborne-sound absorbing element 32 is removed first. The components for foaming the netlike supporting structure unit 18, 91 are then introduced into the mould and the netlike supporting structure unit 18, 19 is foamed.

Instead of inserting the protective outer layer 38 in the first step 200, it is also possible for the protective outer layer 38 to be attached to the casing shell 14, 15 in a further method step, this occurring after the step 203 in which the netlike supporting structure unit 18, 19 is created. The casing shell 14, 14 is first removed from the mould for this purpose, and the protective outer layer 38 is then deposited on the heavy mass element 31 in the form of a lacquer coating, for example.

Figure 5:
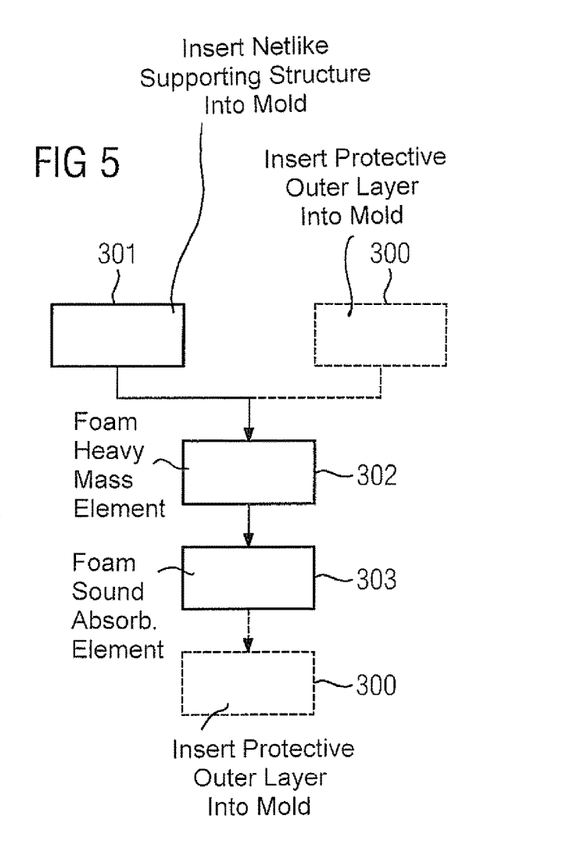
FIG. 5 shows an alternative method to that shown in FIG. 4, for producing a casing shell.

FIG. 5 shows an alternative method to that shown in FIG. 4, for producing the casing shell 100 described in FIG. 3. As in the description of the method in FIG. 4, a mould (not shown) is used for producing the casing shell 100.

In a first step 300, the protective outer layer 38, e.g. the artificial leather layer and/or a thermoplastic and/or a deep-drawable film, etc., is first inserted into the mould. Furthermore, the netlike supporting structure unit 101 is inserted into the mould in a further step 301. The netlike supporting structure unit 101 in this case is composed of a prefabricated component and/or a prefabricated unit, e.g. a netlike supporting structure unit 101 that is produced by an injection molding method and/or a netlike supporting structure unit 101 that is produced from bamboo.

The foaming 302 of the heavy mass element 106 than takes place, wherein the foaming of the heavy mass element 106 takes place using a similar method to that described in FIG. 4. Following the foaming of the heavy mass element 106 101, the netlike supporting structure unit may be at least partially embedded in the foam of the heavy mass element 106.

Following the foaming of the heavy mass element 106, foaming of the airborne-sound absorbing element 107 takes place in a next step 303, wherein the foaming of the airborne-sound absorbing element 107 takes place using a similar method to that described in FIG. 4. During this activity, the netlike supporting structure unit 101 that is connected to the heavy mass element 107 is foamed-in by the airborne-sound absorbing element 107.

The attachment of the netlike supporting structure unit 101 to the heavy mass unit 106 and/or to the airborne-sound absorbing element 107 in this context comprises the steps for inserting the netlike supporting structure unit 101 and the steps for foaming-in the netlike supporting structure unit 101 using the heavy mass element 106 and/or the airborne-sound absorbing element 107.

As described in relation to FIG. 4, the protective outer layer 38 here may likewise be provided after foaming of the casing shell 100 and removal of the casing shell 100 from the mould, e.g. by means of a lacquer coating of the casing shell 100.

While specific embodiments have been described in detail, those with ordinary skill in the art will appreciate that various modifications and alternative to those details could be developed in light of the overall teachings of the disclosure. For example, elements described in association with different embodiments may be combined. Accordingly, the particular arrangements disclosed are meant to be illustrative only and should not be construed as limiting the scope of the claims or disclosure, which are to be given the full breadth of the appended claims, and any and all equivalents thereof. It should be noted that the term "comprising" does not exclude other elements or steps and the use of articles "a" or "an" does not exclude a plurality.

The invention claimed is:

1. A medical imaging device comprising:
a detection unit; and
a housing unit that surrounds said detection unit and includes a casing shell,
wherein the casing shell includes a netlike supporting structure unit and an elastic spring-mass unit,
wherein the netlike supporting structure unit comprises an inner supporting ring and an outer supporting ring, and
wherein the netlike supporting structure unit comprises a plurality of connecting braces that connect the inner supporting ring to the outer supporting ring.

2. The medical imaging device as claimed in claim 1, wherein the elastic spring-mass unit includes an airborne-sound absorbing element and a heavy mass element.

3. The medical imaging device as claimed in claim 2, wherein the heavy mass element is composed at least partially of an integral foam and/or a material that is made of a renewable raw material.

4. The medical imaging device as claimed in claim 2, wherein the heavy mass element is arranged in the form of a layer within the casing shell and has a layer thickness of 2 mm to 5 mm.

5. The medical imaging device as claimed in claim 2, wherein the netlike supporting structure unit is arranged to be at least partially embedded within the airborne-sound absorbing element.

6. The medical imaging device as claimed in claim 2,
wherein the airborne-sound absorbing element includes a layer that is arranged between the heavy mass element and the netlike supporting structure unit, and
wherein said layer has a layer thickness of 3 mm.

7. The medical imaging device as claimed in claim 2,
wherein the casing shell has a region that is arranged between supporting structure elements of the netlike supporting structure unit, and
wherein said region is filled with the airborne-sound absorbing element.

8. The medical imaging device as claimed in claim 1, wherein the netlike supporting structure unit has an integrated shape.

9. The medical imaging device as claimed in claim 1, wherein the netlike supporting structure unit is composed at least partially of an integral foam and/or a material that is made of a renewable raw material.

10. The medical imaging device as claimed in claim 1, wherein the casing shell includes at least one protective outer layer, which is arranged on a side of the spring-mass unit that faces away from the detection unit.

11. The medical imaging device as claimed in claim 1, wherein the casing shell has a shape that curves outwards.

12. The medical imaging device as claimed in claim 1, wherein the casing shell includes a peripheral region with a sealing element.

* * * * *